United States Patent
Weber

[11] Patent Number: 5,571,397
[45] Date of Patent: Nov. 5, 1996

[54] BORON NITRIDE EXHAUST SEAL

[75] Inventor: David C. Weber, Toledo, Ohio

[73] Assignee: Ford Motor Company, Dearborn, Mich.

[21] Appl. No.: 498,446

[22] Filed: Jul. 5, 1995

[51] Int. Cl.⁶ .................................... G01N 27/26
[52] U.S. Cl. .......... 204/428; 204/425; 204/427; 501/96; 501/97; 106/33; 123/672
[58] Field of Search .................. 204/425, 427, 204/428; 501/96, 97; 106/33; 123/672

[56] References Cited

U.S. PATENT DOCUMENTS

| | | | |
|---|---|---|---|
| 4,609,454 | 9/1986 | Ziegler | 204/428 |
| 4,717,464 | 1/1988 | Oshima et al. | 204/428 |
| 4,842,713 | 6/1989 | Stahl | 204/428 |
| 5,031,445 | 7/1991 | Kato et al. | 204/427 |
| 5,089,133 | 2/1992 | Kato et al. | 73/23.31 |
| 5,128,286 | 7/1992 | Funayama et al. | 501/97 |
| 5,228,975 | 7/1993 | Yamada et al. | 204/424 |

*Primary Examiner*—Bruce F. Bell
*Attorney, Agent, or Firm*—Peter Abolins

[57] ABSTRACT

A boron nitride ceramic is used as a high temperature gasket material to prevent gas leakage between an exhaust gas oxygen sensor and the exhaust system of an internal combustion engine.

5 Claims, 1 Drawing Sheet

BORON NITRIDE EXHAUST SEAL

BACKGROUND OF THE INVENTION

1. Field of the Invention

This invention relates to sealing the exhaust gas flow from an internal combustion engine.

2. Prior Art

Using electronic engine control to control an internal combustion engine is known. In particular it is known to use exhaust gas oxygen (EGO) sensors to produce a signal for use by an electronic engine control module.

U.S. Pat. No. 4,842,713 discloses an EGO sensor having a sealing ring 36 made of a soft and deformable metal, such as copper or soft steel. It is also known to use talc to seal of the oxygen sensor as it is screwed into or otherwise fastened into the exhaust gas path. The seal permits proper operation of the exhaust gas oxygen sensor by separating two different gaseous environments.

Limiting gas leakage through the seal keeps hydrocarbons from the exhaust gas out of an air reference cavity which is meant to have a gaseous environment representing the ambient. If leakage exceeds 0.03 cc per minute, the air reference cavity can become tainted and the signal produced by the exhaust gas oxygen sensor which indicates the amount of oxygen in the exhaust gas can be affected. The normal signal ranges from +1 volts DC showing a rich air-to-fuel ratio to 0 volts DC which shows a lean air-to-fuel ratio.

At least three factors can increase the amount of hydrocarbons that leak through the seal into the ambient cavity. The first two factors occur when the engine has been at rest for an extended period of time. The exposure to either gasoline fumes or liquid gasoline particles can increase the leakage. Both seep into the talc which can have an undesirably high gasoline permeability and adsorption. When the exhaust system warms up after start up, the hydrocarbons escape into the air reference cavity as gasoline fumes. The third factor that increases the level of hydrocarbons in the ambient cavity is backpressure. This occurs when the throttle is wide open. The exhaust gas cannot escape the system quickly enough and the pressure backs up from the engine forcing hydrocarbons through the seal.

When leakage exceeds the level at which the signal is affected, the oxygen in the air reference cavity of the oxygen sensor can be depleted and a characteristic shift down can occur. This is a problem in which the signal starts from −1 volts DC when lean and works its way up to 0 volts DC when rich. When an electronic engine control module reads the signal, it assumes that the air-to-fuel ratio is too lean and attempts to rectify the situation by increasing injector pulse width to allow the intake of more fuel into the engine. This adversely affects the emissions. It would be desirable to have a seal with improved electrical isolation and a very low leak rate. These are some of the problems this invention overcomes.

SUMMARY OF THE INVENTION

A boron nitride ceramic is used as a high temperature gasket material in connection with an exhaust gas flow path to prevent gas leaks into or out of an exhaust system of an internal combustion engine. Boron nitride has an advantageously low gas permeability and adsorption.

DETAILED DESCRIPTION OF THE INVENTION

Figure 1:
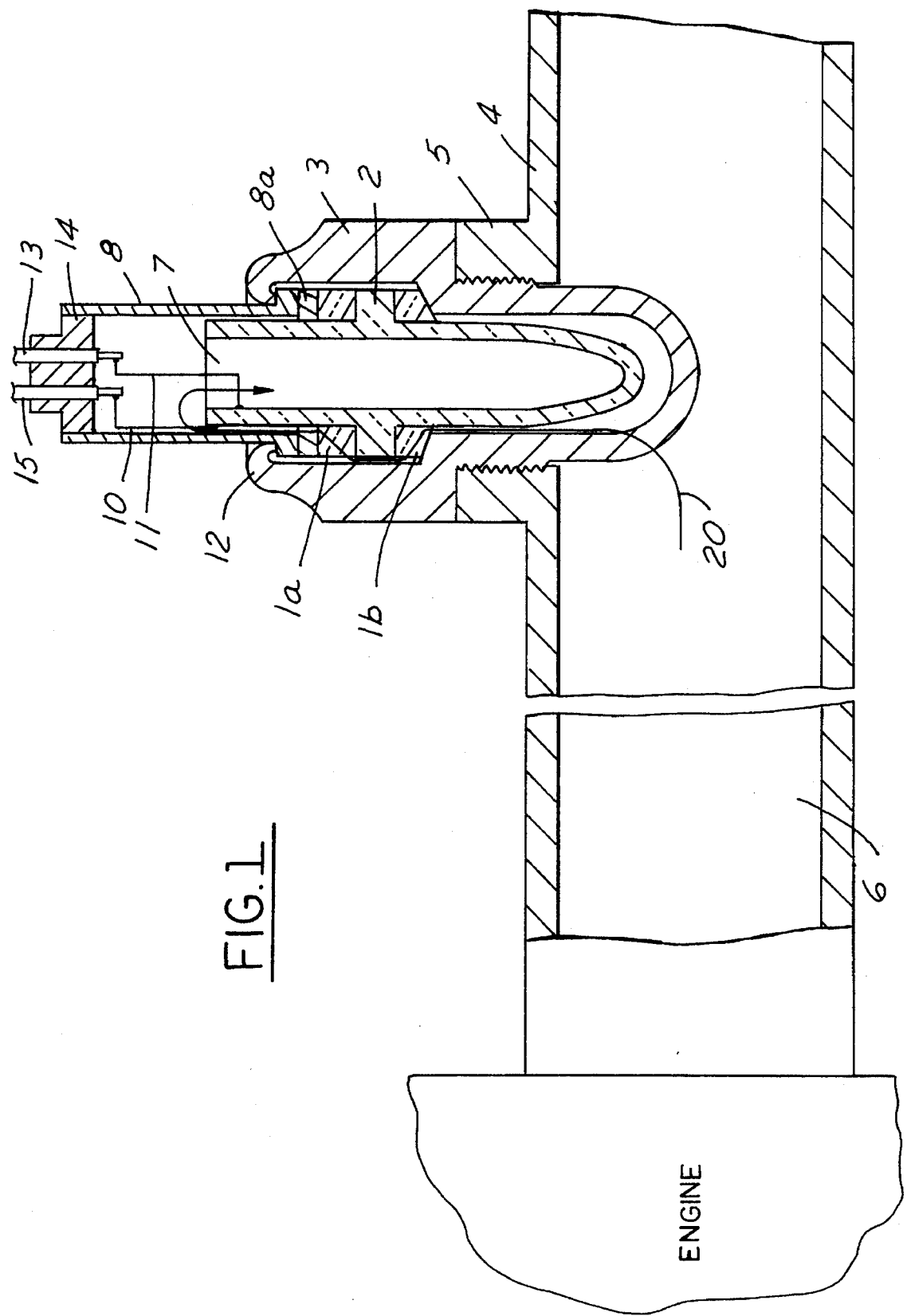
FIG. 1 is a cross sectional view of an exhaust gas oxygen sensor in accordance with an embodiment of this invention.

Boron nitride ceramic is used as an exhaust seal for automotive applications. The material is formed as a cold pressed powder or fired ceramic, is stable in. the operating temperatures of an exhaust system, has high lubricity, has a small deformability, and can have very low gas permeability and adsorption. Boron nitride ceramic can be advantageously used in applications relating to EGR gaskets, exhaust pipe joint gaskets, and manifold gaskets.

The figure shows a simplified section of an exhaust gas oxygen sensor. A tubular zirconia ceramic sensing element 2 is attached to an exhaust pipe 4 by threading a metal shell 3 into a boss 5 in pipe 4. Exhaust gas from a cavity 6 must be sealed from an air reference cavity 7. To do this a gasket 1A, 1B is sealed to sensing element 2 by a mechanical force provided from a plunger 8 and a crimp in shell 3. Sensing element 2 must be completely electrically isolated from metal shell 3. Gasket 1A, 1B or both are composed of primarily boron nitride. A sensor using gasket 1B made of hot pressed, machined boron nitride has a low gas permeability of <0.004 cc per minute. Design validation tests show that the resistance to fuel ingress, fuel vapor characteristics shift down, and air leakage is improved with respect to other known sealing materials such as talc and metal composites.

A metal can (8) protects the reference air (7) from external contaminants. Can (8) may be crimped (12) to a plunger (8a) or welded to a shell (3). On top of can (8) an elaster wire seal (14) keeps contaminants out of the reference air cavity (7), while allowing into the sensor a signal wire (13) and a signal return wire (15). Various connection means are possible from the wires (13, 15) to a sensor element (2). These connections are shown in schematic form as a signal connection (11) and a signal return connection (10). Clean air can be brought to the air reference chamber (7) by either conduction through the porous wires (13, 15) or through a filter (not shown) in can (8) that keeps out water and hydrocarbons. The replenishing of the oxygen in reference air chamber (7) is difficult, because of the necessity to make the sensor water submersible. Therefore, the restricted entry of oxygen makes the sensing element (2) sensitive to the entry of only small amounts of hydrocarbons into the air reference cavity (7). A hydrocarbon pathway is shown as an arrow (20). The hydrocarbons react with the oxygen in the air reference cavity (7) and deplete the free oxygen. This causes free oxygen (typically 20% of cavity (7) volume) to be used up and this affects the sensor signal (i.e. the voltage between the signal and signal return wires (13, 12)). Boron nitride (BN) gaskets 1a and 1b can be reduced to only a gasket 1a or a gasket 1b, if the mechanical force of shell (3) thru the crimp (12) can be made and still keep the outer electrode conductor (10) electrically isolated from the exhaust pipe (4). Thus FIG. 1 shows the permeability and the adsorption properties of gasket (1) to hydrocarbons (arrow 20) are important.

Various modification and variations will no doubt occur to those skilled in the arts to which this invention pertains. Such variations which basically rely on the teachings through which this disclosure has advanced the art are properly considered within the scope of this invention.

I claim:

1. An internal combustion engine having an exhaust gas flow path including a sealing member for restricting the flow of exhaust gas, said sealing member being formed of boron nitride.

2. An exhaust gas oxygen sensor for a internal combustion engine wherein a sealing member is positioned between an air reference cavity and exhaust gas from an exhaust path, said sealing member being formed of boron nitride.

3. An exhaust gas oxygen sensor as recited in claim 2 wherein said sealing member of boron nitride is a hot pressed, machined member having an advantageously high lubricity, low deformability and low gas permeability while operating in the high temperature environment of an exhaust system.

4. An exhaust gas oxygen sensor as recited in claim 2 wherein said sealing member is a cold pressed powder composed predominantly of boron nitride.

5. An exhaust gas oxygen sensor for an internal combustion engine wherein a boron nitride sealing member is positioned between an air reference cavity and exhaust gas from an exhaust path, said sealing member being a hot pressed, machined member having an advantageously high lubricity, low deformability and low gas permeability while operating in the high temperature environment of an exhaust system.

* * * * *